(12) United States Patent
Palti

(10) Patent No.: US 10,893,415 B2
(45) Date of Patent: Jan. 12, 2021

(54) PREVENTING UNAUTHORIZED USE OF DEVICES

(71) Applicant: Yoram Palti, Haifa (IL)

(72) Inventor: Yoram Palti, Haifa (IL)

(73) Assignee: P&P Ultra G Ltd., Haifa (IL)

( * ) Notice: Subject to any disclaimer, the term of this patent is extended or adjusted under 35 U.S.C. 154(b) by 152 days.

(21) Appl. No.: 15/823,882

(22) Filed: Nov. 28, 2017

(65) Prior Publication Data

US 2018/0150624 A1    May 31, 2018

Related U.S. Application Data

(60) Provisional application No. 62/427,225, filed on Nov. 29, 2016.

(51) Int. Cl.
*H04W 12/08* (2009.01)
*G06F 21/32* (2013.01)
(Continued)

(52) U.S. Cl.
CPC ............ *H04W 12/08* (2013.01); *G06F 21/32* (2013.01); *G06F 21/50* (2013.01); *H04L 9/3231* (2013.01);
(Continued)

(58) Field of Classification Search
CPC .......... G06F 21/30; G06F 21/31; G06F 21/32; G06F 21/50; G06F 2221/031;
(Continued)

(56) References Cited

U.S. PATENT DOCUMENTS 4,107,775 A * 8/1978 Ott .................... A61B 5/117
382/115
6,343,140 B1 * 1/2002 Brooks ................ G07C 9/37
382/115
(Continued)

FOREIGN PATENT DOCUMENTS

EP         1064053 A1    1/2001
EP         2966792 A1    1/2016
WO      2018073814 A2    4/2018

OTHER PUBLICATIONS

International Search Report and Written Opinion for PCT/IB2017/057451 dated Feb. 20, 2018.

*Primary Examiner* — Kambiz Zand
*Assistant Examiner* — Mahabub S Ahmed
(74) *Attorney, Agent, or Firm* — Potomac Law Group, PLLC

(57) ABSTRACT

Unauthorized use of a secured device can be prevented using customized hardware that only permits operation of the secured device while an enable signal is being generated, and prevents its operation at all other times. The enable signal is only generated when variations in incoming ultrasound waves indicate that a specific ultrasound activation signal has arrived. This ultrasound activation signal is generated by an activation unit that is acoustically coupled into an ultrasound conductive body (e.g., a person's body). Because the ultrasound activation signal cannot cross air gaps, the ultrasound activation signal will only be able to reach its destination when both the activation unit and the secured device maintain acoustic contact with the ultrasound conductive body. In addition, the signal that is actually received by the secured device must be the same specific ultrasound activation signal that the secured device is expecting to receive.

20 Claims, 4 Drawing Sheets

(51) Int. Cl.
  *G06F 21/50* (2013.01)
  *H04L 9/32* (2006.01)
  *F41A 17/06* (2006.01)
  *A61B 8/00* (2006.01)

(52) U.S. Cl.
  CPC ............... *A61B 8/00* (2013.01); *F41A 17/06* (2013.01); *G06F 2221/031* (2013.01)

(58) Field of Classification Search
  CPC ........ H04L 9/3231; A61B 8/00; H04W 12/08; F41A 17/06; F41A 17/04; F41A 17/08
  USPC .......................................................... 726/27
  See application file for complete search history.

(56) References Cited

U.S. PATENT DOCUMENTS

| | | | | |
|---|---|---|---|---|
| 6,678,984 | B1* | 1/2004 | Rapp | F41A 17/066 42/70.01 |
| 8,908,894 | B2* | 12/2014 | Amento | H04R 25/554 381/326 |
| 9,405,892 | B2* | 8/2016 | Baldwin | G06F 21/32 |
| 9,424,456 | B1* | 8/2016 | Kamath Koteshwara | G06K 9/00093 |
| 9,622,718 | B2* | 4/2017 | Watanabe | G01S 7/5205 |
| 10,296,734 | B2* | 5/2019 | Johnston | G06F 21/32 |
| 2003/0098774 | A1* | 5/2003 | Chornenky | G07C 9/37 340/5.1 |
| 2004/0202339 | A1 | 10/2004 | O'Brien et al. | |
| 2005/0054926 | A1* | 3/2005 | Lincoln | G06K 9/0002 600/443 |
| 2005/0257411 | A1* | 11/2005 | Wootton | F41A 17/063 42/70.01 |
| 2007/0055888 | A1* | 3/2007 | Miller | G06F 21/32 713/186 |
| 2008/0071328 | A1 | 3/2008 | Haubrich et al. | |
| 2008/0125834 | A1* | 5/2008 | Hendrix | A61N 5/0616 607/88 |
| 2008/0214935 | A1* | 9/2008 | Levin | H04L 63/0861 600/442 |
| 2008/0223926 | A1* | 9/2008 | Miller | G07C 9/37 235/382 |
| 2008/0229409 | A1* | 9/2008 | Miller | G06F 21/32 726/19 |
| 2009/0007476 | A1* | 1/2009 | Mauch | F41A 17/063 42/1.01 |
| 2009/0213087 | A1* | 8/2009 | Abdallah | H04N 21/25875 345/173 |
| 2009/0270949 | A1 | 10/2009 | Kalpin et al. | |
| 2009/0313049 | A1* | 12/2009 | Joao | G16H 80/00 705/3 |
| 2011/0113664 | A1* | 5/2011 | Delgado Acarreta | F41A 17/06 42/70.11 |
| 2012/0150091 | A1* | 6/2012 | Roger | A61M 1/3639 604/6.16 |
| 2013/0173926 | A1* | 7/2013 | Morese | G06F 21/32 713/186 |
| 2013/0184587 | A1* | 7/2013 | Eom | G16H 30/40 600/443 |
| 2014/0085460 | A1* | 3/2014 | Park | G09G 3/001 348/135 |
| 2014/0279528 | A1* | 9/2014 | Slaby | G06F 21/32 705/44 |
| 2015/0082890 | A1* | 3/2015 | Pant | G01N 29/265 73/618 |
| 2015/0109104 | A1* | 4/2015 | Fadell | H04L 67/12 340/5.65 |
| 2015/0269574 | A1* | 9/2015 | Peng | G06Q 20/401 705/77 |
| 2016/0063232 | A1* | 3/2016 | Seol | G04G 21/08 726/19 |
| 2016/0070900 | A1* | 3/2016 | Kim | G06F 21/34 726/3 |
| 2016/0246396 | A1* | 8/2016 | Dickinson | G06K 9/00107 |
| 2016/0277925 | A1* | 9/2016 | Bengtsson | H04L 63/083 |
| 2016/0278740 | A1* | 9/2016 | Negrila | G16H 40/63 |
| 2017/0011210 | A1* | 1/2017 | Cheong | G06F 21/32 |
| 2017/0035327 | A1* | 2/2017 | Yuen | A61B 5/7264 |
| 2017/0075700 | A1* | 3/2017 | Abudi | G06F 9/4406 |
| 2017/0118639 | A1* | 4/2017 | Beale | H04W 12/06 |
| 2017/0295014 | A1* | 10/2017 | Baras | G06K 9/00006 |
| 2017/0347993 | A1* | 12/2017 | Anand | A61B 8/585 |
| 2018/0018838 | A1* | 1/2018 | Fankhauser | G06K 19/06046 |
| 2018/0060635 | A1* | 3/2018 | Li | G06T 5/006 |
| 2018/0063126 | A1* | 3/2018 | Karapantelakis | G06Q 20/3272 |
| 2018/0101711 | A1* | 4/2018 | D'Souza | G06K 9/228 |
| 2018/0115797 | A1* | 4/2018 | Wexler | H04L 51/32 |
| 2018/0121643 | A1* | 5/2018 | Talwerdi | G06F 21/33 |
| 2018/0198623 | A1* | 7/2018 | Hoffman | A61B 5/027 |
| 2018/0232512 | A1* | 8/2018 | Razouane | G06F 16/21 |
| 2018/0348853 | A1* | 12/2018 | Shchur | G06F 21/32 |
| 2019/0089539 | A1* | 3/2019 | Dupont | G06K 9/00107 |
| 2019/0102662 | A1* | 4/2019 | Snell | G06K 19/07754 |
| 2019/0102665 | A1* | 4/2019 | Snell | G06K 19/07747 |

* cited by examiner

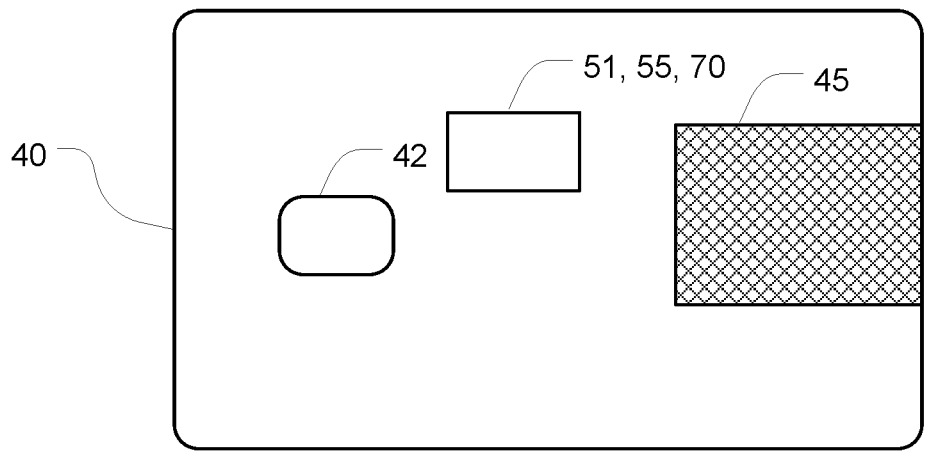
FIG. 4
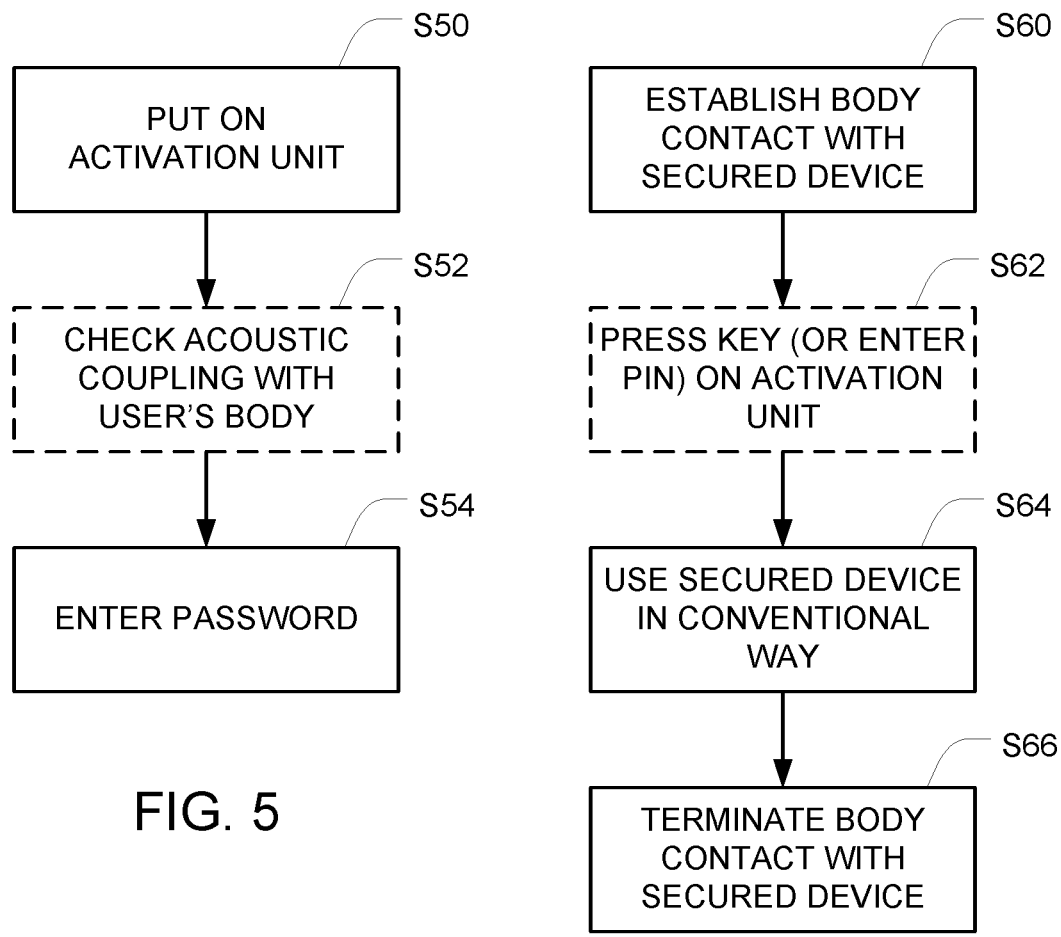
FIG. 5
FIG. 6

PREVENTING UNAUTHORIZED USE OF DEVICES

CROSS REFERENCE TO RELATED APPLICATIONS

This Application claims the benefit of U.S. Provisional Application 62/427,225 filed Nov. 29, 2016, which is incorporated herein by reference in its entirety.

BACKGROUND

In many circumstances, it is desirable to prevent unauthorized persons from using certain devices. Examples of such devices include credit cards, cell phones, computers, hand guns, etc. But existing approaches for restricting usage to authorized persons are problematic because they are not always effective and often impose an undue burden on the authorized users.

SUMMARY OF THE INVENTION

Unauthorized use of a secured device can be prevented using customized hardware that only permits operation of the secured device while an enable signal is being generated. The enable signal is only generated when variations in incoming ultrasound waves indicate that a specific ultrasound activation signal has arrived. Because the ultrasound activation signal cannot cross air gaps, the ultrasound activation signal will only be able to reach its destination when both the activation unit and the secured device maintain acoustic contact with the ultrasound conductive body. In addition, the signal that is actually received by the secured device must be the same specific ultrasound activation signal that the secured device is expecting to receive.

One aspect of the invention is directed to a first system for preventing unauthorized use of a secured device. The first system comprises an activation unit and a secured device. The activation unit includes a first ultrasound transducer positioned to acoustically couple with an ultrasound conductive body when the activation unit is placed in contact with the ultrasound conductive body, and an ultrasound signal generator configured to drive the first ultrasound transducer. The first ultrasound transducer and the ultrasound signal generator are configured such that when (a) the first ultrasound transducer is acoustically coupled with the ultrasound conductive body and (b) the ultrasound signal generator drives the first ultrasound transducer, the first ultrasound transducer will transmit an ultrasound activation signal into the ultrasound conductive body. The secured device includes hardware that performs a function; and a second ultrasound transducer positioned to acoustically couple with the ultrasound conductive body prior to use of the secured device, and to generate an output signal responsive to ultrasound energy arriving at the second ultrasound transducer. The secured device also includes an ultrasound receiver that (a) receives the output signal generated by the second ultrasound transducer and (b) generates an enable signal when variations in the output signal generated by the second ultrasound transducer indicate that the ultrasound activation signal has arrived at the second ultrasound transducer; and an interface circuit that receives the enable signal. The interface circuit is configured to (a) allow the hardware to perform the function when the enable signal arrives and (b) prevent the hardware from performing the function when the enable signal has not arrived.

In some embodiments of the first system, the ultrasound signal generator drives the first ultrasound transducer in a manner that embeds a code into the ultrasound activation signal, and the ultrasound receiver generates the enable signal when variations in the output signal indicate that the code is present in the ultrasound activation signal. In some of these embodiments, the ultrasound signal generator comprises a first controller that is programmed to impart the code and the ultrasound receiver comprises a second controller that that is programmed to recognize when the code is present. In some of these embodiments, the activation unit further includes a user interface, and the first controller is further programmed to wait for unlocking via the user interface before imparting the code. In some of these embodiments, the unlocking comprises entry of a password or biometric information via the user interface.

In some embodiments of the first system, the enable signal persists for a predetermined time after the ultrasound activation signal has arrived at the second ultrasound transducer. In some embodiments of the first system, the ultrasound activation signal comprises a sequence of codes, and the enable signal terminates immediately when the sequence of codes ceases to arrive at the second ultrasound transducer.

In some embodiments of the first system, the ultrasound activation signal has a frequency between 100 kHz and 5 MHz. In some embodiments of the first system, the ultrasound activation signal has a frequency between 1 MHz and 2 MHz.

In some embodiments of the first system, the secured device comprises a firearm and the interface circuit is configured to (a) allow the firearm to fire when the enable signal arrives and (b) prevent the firearm from firing when the enable signal has not arrived. In some of these embodiments, the interface circuit comprises a solenoid having a first position that prevents the firearm from firing and a second position that allows the firearm to fire, and the interface circuit controls the position of the solenoid in response to the enable signal.

In some embodiments of the first system, the secured device comprises a financial transaction card, and the interface circuit is configured to (a) permit use of the financial transaction card when the enable signal arrives and (b) prevent use of the financial transaction card when the enable signal has not arrived. In some embodiments of the first system, the secured device comprises a computer, and the interface circuit is configured to (a) permit use of the computer when the enable signal arrives and (b) prevent use of the computer when the enable signal has not arrived. In some embodiments of the first system, the secured device comprises a mobile phone, and the interface circuit is configured to (a) permit use of the mobile phone when the enable signal arrives and (b) prevent use of the mobile phone when the enable signal has not arrived.

Another aspect of the invention is directed to a first apparatus for preventing unauthorized use of a secured device. The first apparatus comprises hardware that performs a function; and an ultrasound transducer positioned to acoustically couple with an ultrasound conductive body prior to use of the secured device, and to generate an output signal responsive to ultrasound energy arriving at the ultrasound transducer. The first apparatus also comprises an ultrasound receiver that (a) receives the output signal generated by the ultrasound transducer and (b) generates an enable signal when variations in the output signal generated by the ultrasound transducer indicate that an ultrasound activation signal has arrived at the ultrasound transducer; and an interface circuit that receives the enable signal. The interface circuit is configured to (a) allow the hardware to perform the function when the enable signal arrives and (b) prevent the hardware from performing the function when the enable signal has not arrived.

In some embodiments of the first apparatus, the ultrasound receiver generates the enable signal when variations in the output signal indicate that an expected code is present in the ultrasound activation signal.

In some embodiments of the first apparatus, the enable signal persists for a predetermined time after the ultrasound activation signal has arrived at the ultrasound transducer.

In some embodiments of the first apparatus, the ultrasound activation signal comprises a sequence of codes, and the enable signal terminates immediately when the sequence of codes ceases to arrive at the ultrasound transducer.

Another aspect of the invention is directed to a first method for preventing unauthorized use of a device. The first method comprises generating an output signal responsive to ultrasound energy arriving at an ultrasound transducer; generating an enable signal when variations in the output signal indicate that an ultrasound activation signal has arrived at the ultrasound transducer; preventing the device from operating until the enable signal is generated; and permitting operation of the device while the enable signal is being generated.

In some embodiments of the first method, the ultrasound activation signal comprises a coded message.

In some embodiments of the first method, the enable signal persists for a predetermined time after the ultrasound activation signal has arrived at the ultrasound transducer.

BRIEF DESCRIPTION OF THE DRAWINGS

FIG. 4 depicts an embodiment in which the secured device is a financial transaction card.

FIG. 5 depicts a flowchart for initializing the activation unit of the FIG. 1 embodiment.

FIG. 6 depicts a flowchart for using the secured device of the FIG. 1 embodiment.

DESCRIPTION OF THE PREFERRED EMBODIMENTS

Figure 1:
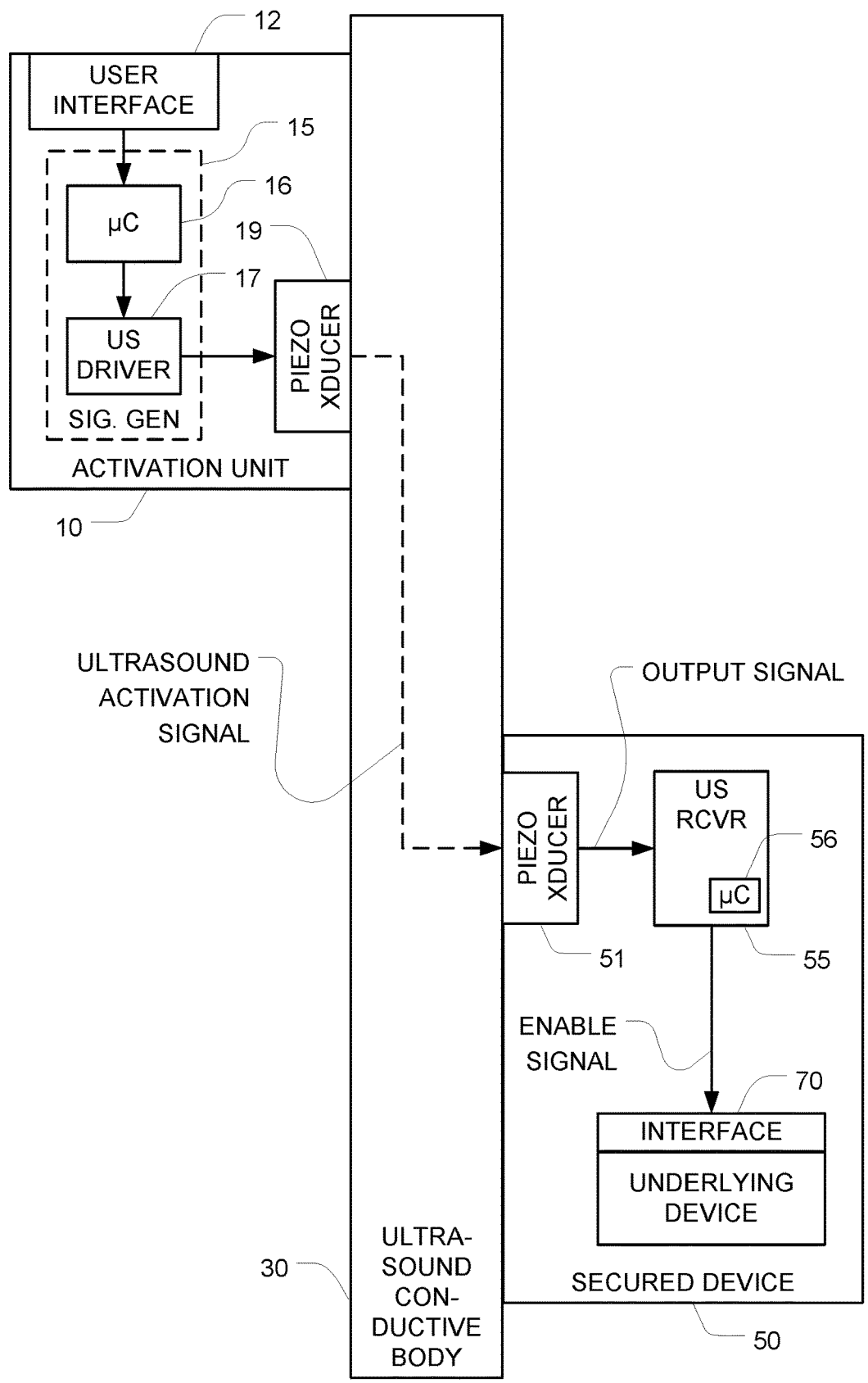
FIG. 1 is a block diagram of a system for preventing unauthorized use of a secured device.

FIG. 1 is a block diagram of a system for preventing unauthorized use of a secured device. The system includes two parts: an activation unit 10 and the secured device 50. The secured device 50 is disabled by default, and will only be activated when it receives an ultrasound activation signal.

The ultrasound activation signal is generated by the activation unit 10, and it is acoustically coupled into the ultrasound conductive body 30. The activation signal then travels through the ultrasound conductive body 30, and is acoustically coupled into the secured device 50. If either of those two acoustic couplings is not present (which happens, for example, if an air gap is introduced into the path of the ultrasound activation signal), the ultrasound activation signal will not arrive at the secured device 50, and the secured device 50 will remain disabled. In addition, if the activation unit 10 fails to generate the ultrasound activation signal or generates an incorrect ultrasound activation signal, the secured device 50 will not be activated (and will remain disabled).

The secured device 50 includes the underlying device itself 75 and also incorporates additional components 51, 55, 70 that have the ability to enable or disable the underlying device. One of these additional components is an ultrasound transducer 51 (referred to herein as the second ultrasound transducer), and the device 75 is ultimately enabled or disabled depending on whether appropriate signals are arriving at this ultrasound transducer 51 (as described in greater detail below). The secured device 50 is configured so that the underlying device 75 is disabled by default. But when the activation signal is received by the second ultrasound transducer 51, the secured device 50 will enable the underlying device 75.

The activation unit 10 includes an ultrasound signal generator 15 and a first ultrasound transducer 19. As described in greater detail below, the first ultrasound transducer 19 generates the activation signal that will ultimately be used by the secured device 50 to enable the underlying device 75.

The use of ultrasound to convey the activation signal from the first ultrasound transducer 19 (in the activation unit 10) to the second ultrasound transducer 51 (in the secured device 50) is very important because many frequencies of ultrasound signal cannot traverse air gaps. More specifically, most solid and liquids (including but not limited to plastic, metal, and human bodies) are a good conductors of ultrasound energy. For ultrasound waves of frequencies above 100 kHz (e.g., between 100 kHz and 5 MHz), the mechanical impedance of both the ultrasound conductive body 30 and the body of the secured device 50 (which will typically be metal, plastic or another solid) is very different from that of the ambient air.

Because of this difference in impedance, if any air gaps exist in the path between the first ultrasound transducer 19 and the second ultrasound transducer 51, the ultrasound activation signal that originates from the first ultrasound transducer 19 will not be able to reach the second ultrasound transducer 51. This is because the large impedance mismatches introduced by the air gaps cause complete reflection of the ultrasound waves, and prevents the ultrasound activation signal from reaching its intended destination (i.e., the second ultrasound transducer 51). For example, the mechanical impedance of water is about 400 times higher than the mechanical impedance of air. This mismatch results in transmission of less than 0.1% of the energy across any air gap that may exist between the first ultrasound transducer 19 and the second ultrasound transducer 51. Note also that the mechanical impedance of human tissue and most solids (e.g., most metals and plastics) are all fairly close to that of water, and very different from air.

On the other hand, when no air gaps exist in the path between the activation unit 10 and the secured device 50, it becomes possible for the ultrasound activation signal to travel between those two devices. The FIG. 1 embodiment takes advantage of this by providing a path between the activation unit 10 and the secured device 50 that includes no air gaps, and relying on this path to convey an ultrasound activation signal between the activation unit 10 and the secured device 50. Notably, this path traverses one physical boundary between the activation unit 10 and the ultrasound conductive body 30, and also traverses a second physical boundary between the ultrasound conductive body 30 and the secured device 50. But because the impedances on both sides of each of those boundaries are in the same ballpark, a significant portion of the ultrasound signal will be able to traverse those boundaries. As a result, when this path exists, the activation signal can travel from the activation unit 10 to the secured device 50 and enable the underlying device 75. But whenever this path is interrupted, the activation signal cannot reach the secured device 50, and the secured device 50 will revert to its default disabled condition.

The FIG. 1 embodiment relies on a gapless path for the ultrasound activation signal between the first ultrasound transducer 19 and the second ultrasound transducer 51. More specifically, if the activation unit 10 is positioned so that the first ultrasound transducer 19 is acoustically coupled with the ultrasound conductive body 30 when the activation unit 10 is placed in contact with the ultrasound conductive body 30, then ultrasound signals that emanate from the first ultrasound transducer 19 will be able to enter the ultrasound conductive body 30 and travel through that body 30. Optionally, the acoustic coupling between the first ultrasound transducer 19 and the ultrasound conductive body 30 may be improved using an ultrasound conductive gel. Similarly, if the secured device 50 is positioned so that the second ultrasound transducer 51 is acoustically coupled with the ultrasound conductive body 30, then ultrasound signals that are traveling through that body 30 will be able to arrive at the second ultrasound transducer 51.

The second ultrasound transducer 51 is preferably a piezoelectric element that converts ultrasound frequency mechanical vibrations into an electrical output signal. When the ultrasound activation signal arrives at the second ultrasound transducer 51, the second ultrasound transducer 51 will generate an output signal responsive to the arriving ultrasound vibrations. An ultrasound receiver 55 (a) receives the output signal generated by the second ultrasound transducer 51 and (b) generates an enable signal when variations in the output signal generated by the second ultrasound transducer 51 indicate that the ultrasound activation signal has arrived at the second ultrasound transducer 51.

In the simplest case, the ultrasound receiver 55 can perform a simple analog amplification of the output signal that arrives from the second ultrasound transducer 51, and generate the enable signal when the amplitude exceeds a predetermined threshold. In alternative embodiments, the ultrasound receiver 55 can detect the presence of a particular frequency of ultrasound and generate the enable signal when the amplitude in that frequency band exceeds a predetermined threshold. In alternative embodiments, the ultrasound receiver 55 can be configured to detect pulses and/or modulated waveforms.

In some embodiments, the transmission from the activation unit 10 to the secured device 50 uses an ultrasound wave as a carrier and modulates information onto that carrier. In these situations, the ultrasound receiver 55 can be designed to generate the enable signal only when the expected data arrives via the ultrasound carrier. Examples of suitable modulation schemes include but are not limited to analog modulation schemes (e.g., AM, FM, PM, etc.), analog modulation schemes (e.g., PPM, PSK, FSK, etc.) and spread spectrum schemes (e.g., CSS, etc.). A wide variety of alternative modulation approaches can be readily envisioned. These embodiments preferably incorporate intelligence into the ultrasound receiver 55 using, for example a microprocessor or microcontroller 56 that is suitably programmed to recognize when the expected data has arrived. The microprocessor or microcontroller 56 is programmed to generate the enable signal when the expected data arrives and to refrain from generating the enable signal in all other situations. Optionally, the data arriving at microprocessor or microcontroller 56 may be encrypted, in which case the microprocessor or microcontroller 56 should decrypt that data.

An interface circuit 70 receives the enable signal. The interface circuit 70 is configured to allow the hardware 75 to perform its function when the enable signal arrives, and to prevent the hardware 75 from performing its function in all other situations. The nature of the interface circuit 70 will depend on the nature of the underlying hardware 75. For example, when the secured device 50 is a financial transaction card (e.g., a credit card or a debit card that includes a smart chip) the interface circuit could be a microcontroller that is configured to send a signal to the smart chip that only permits use of the financial transaction card when the enable signal arrives. In situations where the financial transaction card already includes a microcontroller, the functionality of the interface circuit 70 may optionally be incorporated into the included microcontroller.

In another example, when the secured device 50 is a firearm, the interface circuit would be configured to allow the firearm to fire when the enable signal arrives and prevent the firearm from farm firing when the enable signal has not arrived. This may be accomplished, for example, using a solenoid that can be switched between a first position that disables the firearm and a second position that enables the firearm in response to the absence or presence of the enable signal, respectively. Notably, the underlying device is not limited to financial transaction card and firearms. To the contrary, the system depicted in FIGS. 1-3 may be used to enable or disabled a wide variety of alternative underlying devices. Of course, the design of the interface circuit for any given underlying device will vary depending on the specific nature of that underlying device. But in most cases, the design of the interface circuit will be relatively straightforward.

The activation unit 10 generates the ultrasound activation signal that is expected by the ultrasound receiver 55 in the secured device 50. Accordingly, the design of the activation unit 10 will depend on the design of the ultrasound receiver 55, as will be appreciated by persons skilled in the relevant arts. For example, if the ultrasound receiver 55 is configured to detect the presence of a particular frequency of ultrasound, the activation unit 10 should generate an ultrasound activation signal at that frequency. Frequencies greater than 100 kHz (e.g., between 100 kHz and 5 MHz) are preferred. In some embodiments, frequencies between 1 and 2 MHz are used. These preferred frequencies provide both good depth of penetration within the ultrasound conductive body 30 and a large impedance mismatch whenever an air gap is introduced into the path of the ultrasound activation signal.

Similarly, if the ultrasound receiver 55 is configured to generate the enable signal when it receives a predetermined code word that is encoded onto the ultrasound activation signal using pulse position modulation, the activation unit 10 should generate an ultrasound activation signal that includes the expected codeword and uses the expected modulation scheme. The activation unit 10 includes a signal generator 15 that drives the first ultrasound transducer 19 with an ultrasound frequency signal. In some embodiments, the signal generator 15 can be a simple sinusoidal oscillator. In alternative embodiments (e.g., when codewords are imparted onto an ultrasound carrier), the signal generator 15 can be designed using a microcontroller 16 that controls an ultrasound driver 17 and causes the ultrasound driver to drive the first ultrasound transducer 19 so that it will generate the ultrasound activation signal that is expected by the ultrasound receiver 55, including any specific codewords and/or encryption schemes that are expected by the ultrasound receiver 55.

When the first ultrasound transducer 19 is acoustically coupled with the ultrasound conductive body 30, and the ultrasound signal generator 15 drives the first ultrasound transducer, the first ultrasound transducer 19 will transmit an ultrasound activation signal into the ultrasound conductive body 30.

In some embodiments, the activation unit 10 also includes a user interface 12 that can be used to provide an additional layer of security. For example, the activation unit 10 can be programmed not to generate the ultrasound activation signal until the activation unit is unlocked by entering a password via the user interface 12. In alternative embodiments, the user interface 12 can include a biometric sensor (e.g., a fingerprint sensor), and the controller 16 in the signal generator 15 can be programmed not to generate the expected ultrasound activation signal until a particular fingerprint has been detected by the fingerprint sensor. These features reduce the chance that an unauthorized person who manages to get hold of both the activation unit 10 and the secured device 50 will be able to use the secured device 50.

The activation unit 10 may be configured to remain dormant until it receives a wakeup signal (e.g., via the user interface 12). This will help extend the battery life in the activation unit 10.

The situation depicted in FIG. 1 (in which the signal travels from the first ultrasound transducer 19 to the second ultrasound transducer 51 via the ultrasound conductive body 30) is based on the stated conditions that the first ultrasound transducer 19 is acoustically coupled with the ultrasound conductive body 30 and that the second ultrasound transducer 51 is also acoustically coupled with the ultrasound conductive body 30. These two points of acoustic coupling, taken together with the fact that the ultrasound activation signal can travel through the ultrasound conductive body 30 allow the ultrasound energy emanating from the first ultrasound transducer 19 to reach the second ultrasound transducer 51.

But as soon as any one of those points of acoustic coupling is disturbed, the ultrasound activation signal will no longer be able to traverse the entire path between the first ultrasound transducer 19 to the second ultrasound transducer 51, and will never arrive at the second ultrasound transducer 51. One example of disrupted coupling appears in FIG. 2, in which the activation unit 10 is not acoustically coupled with the ultrasound conductive body 30. In this scenario, the ultrasound activation signal generated in the activation unit 10 is not coupled into the ultrasound conductive body 30. As a result, it will never arrive at the secured device 50, so the secured device will remain disabled. Another example of disrupted coupling appears in FIG. 3 in which the secured device 50 is not acoustically coupled with the ultrasound conductive body 30. In this scenario, the ultrasound activation signal generated in the activation unit 10 is coupled into the ultrasound conductive body 30 and travels through that body. However, because the secured device 50 is not acoustically coupled to the ultrasound conductive body 30, the ultrasound activation signal will not reach the secured device 50, and the secured device will remain disabled. Note that the scenario depicted in FIG. 3 also provides protection against unauthorized use of a lost or stolen secured device 50. For if the secured device 50 is lost or stolen, it will necessarily be separated from the owner's body. As a result, the ultrasound activation signal generated by the activation unit 10 that is positioned against the owner's body will not be able to reach the lost or stolen secured device 50, and that device will remain disabled.

As explained above, FIGS. 1-3 depict three distinct situations. When both the activation unit 10 and the secured device 50 are in acoustic contact with the ultrasound conductive body 30 (as seen in FIG. 1), the ultrasound activation signal will reach the second ultrasound transducer 51 in the secured device 50, and the secured device 50 will activate the underlying hardware 75. But when either the activation unit 10 or the secured device 50 break acoustic contact with the ultrasound conductive body 30 (as seen in FIGS. 2 and 3, respectively) the ultrasound activation signal will not reach the second ultrasound transducer 51 in the secured device 50, and the secured device 50 will not activate the underlying hardware 75.

Figure 2:
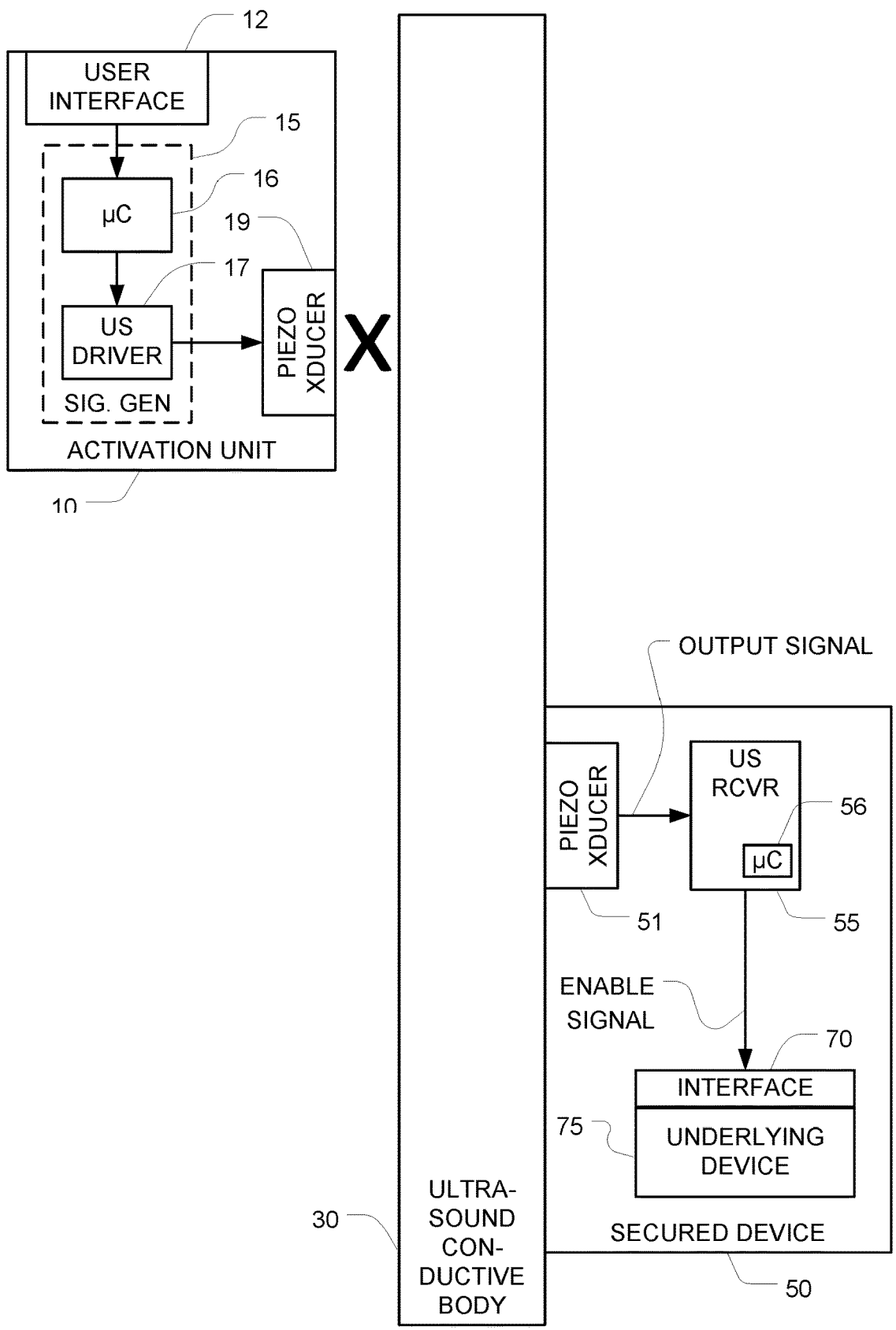
FIG. 2 depicts the FIG. 1 embodiment when an activation signal is interrupted at one location.
Figure 3:
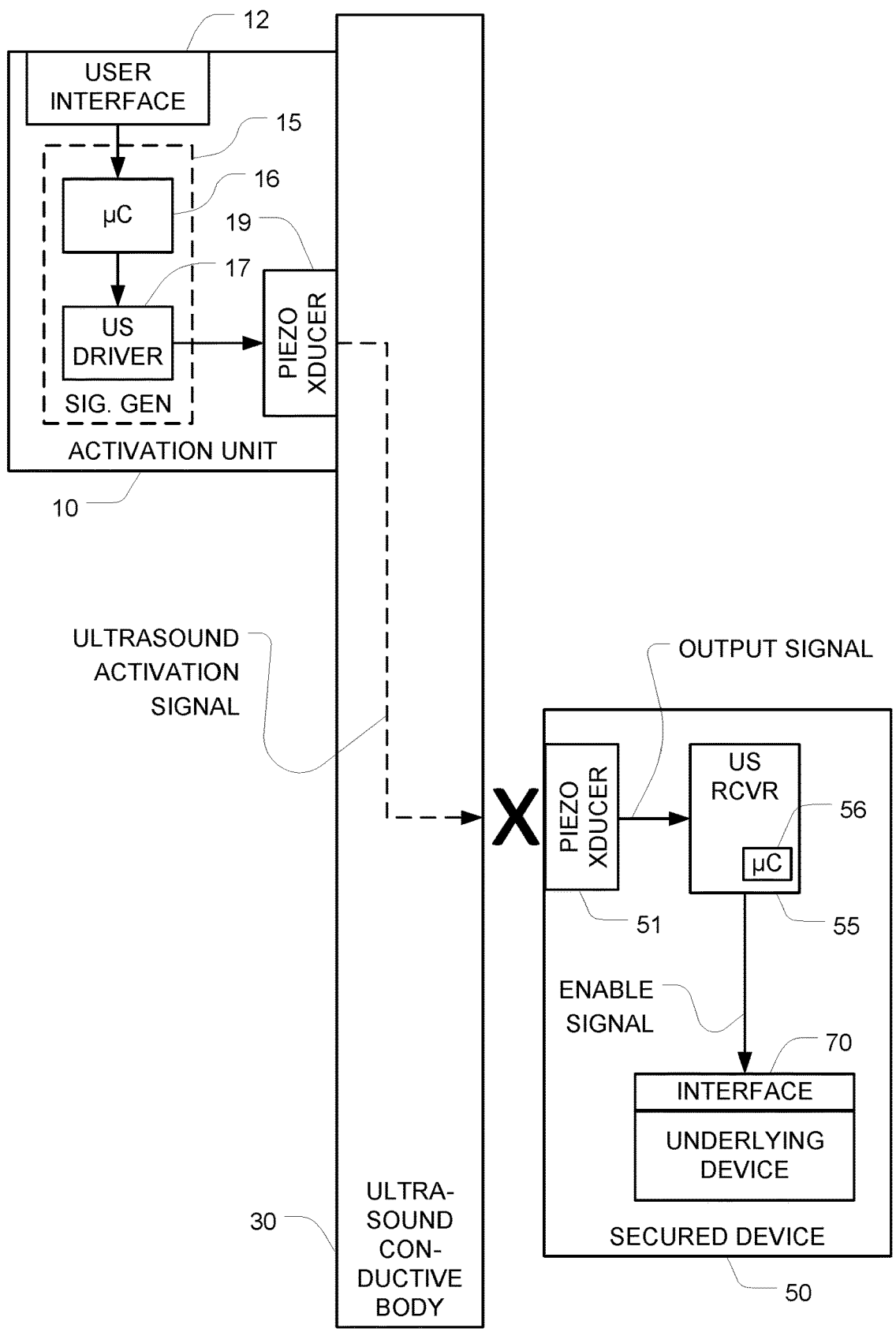
FIG. 3 depicts the FIG. 1 embodiment when an activation signal is interrupted at another location.

Because the human body conducts ultrasound, the system depicted in FIGS. 1-3 can be used to prevent unauthorized use of a wide variety of hand held or body-mounted secured devices. In this context, the activation unit 10 could be incorporated into a housing that is worn against the user's body, similar to a wristwatch. In this situation, the only person who will be able to activate the secured device 50 will be the person who is wearing the wristwatch-mounted activation unit 10.

FIG. 4 depicts one such example in which the secured device is a financial transaction card 40 (e.g., a credit card or a debit card). The card 40 should be constructed with at least one region 45 (e.g., a flat pad) that permits acoustic coupling to the second ultrasound transducer 51, and also includes an ultrasound receiver 55 and interface 70 (all shown in FIG. 1). The card 40 also includes a smart chip 42 that performs all of the operations of a conventional credit card smart chip, but has been modified to permit enabling/disabling based on an enable signal received from interface hardware 70. If an authorized user is wearing the wristwatch-mounted activation unit 10 places his or her thumb on the pad 45 while swiping the card through a conventional card reader, the ultrasound activation signal will be able to travel from the activation unit 10, through the user's body, and into the financial transaction card 40, in order to enable the financial transaction card. But if a stranger finds the card a few minutes later and tries to use it, the card 40 will not work because it will not be receiving the ultrasound activation signal.

In another example, the secured device 50 could be a computer, a mobile phone, or a tablet. The device should be constructed with at least one region (e.g., a flat pad) that permits acoustic coupling to the second ultrasound transducer 51, and also includes an ultrasound receiver 55 and interface 70 (all shown in FIG. 1). The placement of this region will depend on the context of the device. For example, the pad could be positioned on the same panel that houses the keyboard and the touchpad on a laptop computer, or on the rear face or the side panel of a mobile phone or a tablet. The components 51-70 depicted in FIGS. 1-3 will all be incorporated into the body of the device, and the device is programmed (e.g., in BIOS or in the operating system) to interact with those components 51-70 to provide the security features described herein in addition to all of the device's usual functions (which will depend on the nature of the device). More specifically, the device is constructed and programmed to perform all of its ordinary functions and also to permit enabling/disabling based on an enable signal received from the interface hardware 70. If an authorized user wearing or holding the activation unit 10 places his or her finger on the pad, the ultrasound activation signal will be able to travel from the activation unit 10, through the user's body, and into the device, in order to enable the device. But if a stranger finds or steals the device and tries to use it, the device will not work because the pad will not be receiving the ultrasound activation signal.

In another example, the secured device 50 could be a firearm. The firearm should be constructed with at least one region (e.g., the butt of the gun) that permits acoustic coupling to the second ultrasound transducer 51. If an authorized user is wearing the wristwatch-mounted activation unit 10 while holding the gun by its butt, the ultrasound activation signal will be able to travel from the activation unit 10, through the user's body, and into the gun, in order to enable firing of the gun. But if the authorized user drops the gun and another person picks it up, the gun will not fire because it will not be receiving the ultrasound activation signal.

The timing of the enable signal generated by the ultrasound receiver 55 in the secured device 50 can be varied depending on context. For example, in the context of a financial transaction card, the ultrasound receiver 55 can be programmed (e.g., by programming the microprocessor or microcontroller 56) to maintain the enable signal for a predetermined window of time (e.g., 2 minutes) after the ultrasound activation signal has arrived. This would permit an authorized card user to enable his card (e.g., by placing his thumb on the pad and activating the user interface 12 on the activation unit 10) and then hand the card to another person, such as a waiter at a restaurant. The waiter would then be able to use the card during the predetermined window of time. But once the predetermined window of time has expired (e.g., if the waiter forgets to return the card to the authorized user), the secured device 50 would return to its default disabled state.

Alternatively, in the context of a handgun, the ultrasound activation signal preferably comprises a periodic sequence of codes (e.g., one code every 50 mSec), and the receiver 55 is preferably hardwired or programmed to terminate the enable signal immediately after any code in the sequence fails to arrive. Thus, as long as authorized user is holding the gun, the receiver 55 will continue to generate the enable signal, and the gun can be fired. But within 50 mSec after the authorized user releases the gun, the next code in the periodic sequence will fail to reach the receiver 55, and the receiver 55 will terminate the enable signal (thereby rendering the gun unusable).

FIGS. 5 and 6 depict one example of an approach for operating the activation unit 10 and the secured device 50 in the FIG. 1 embodiment. In this example, the activation unit 10 is activated by having the user enter a password. In step S50, the user puts on the activation unit (e.g., by strapping it on to his wrist). Optionally, step S52 may be implemented to have the activation unit check the acoustic coupling between the activation unit and the user's body. (If poor coupling is detected, the activation unit can display an appropriate error message.) In step S54, the user enters a password into the user interface of the activation unit. At this point, the activation unit is prepared to send the ultrasound activation signal into the secured device. Note that steps S50-S54 need only be performed once per day (e.g., when the user straps the activation unit on in the morning). Optionally, the activation unit may be programmed to disable itself off automatically when contact between the activation unit and with the user's body has been broken. In this case, the password would have to be re-entered after contact is eventually reestablished.

When the user wants to use the secured device, he establishes body contact with the secured device in step S60, e.g., by holding his finger against a designated pad on the device (e.g., pad 45 in FIG. 4). At this point, the ultrasound activation signal can travel from the activation unit 10 to the secured device 50 (both shown in FIG. 1) via the user's body as described above, which permits the user to use the secured device in its conventional way in step S64. (For example, in the case of a credit card, the user could swipe the card through a card reader.) Optionally, an additional step S62 may be required prior to each use of the device. When this option is implemented, the user must press a key or enter a PIN on the activation unit before the activation unit will transmit the ultrasound activation signal. (Notably, this option will use less battery power than a configuration that continuously or periodically transmits ultrasound.) After the ultrasound activation signal has been transmitted, the secured device 50 will be enabled, and the user uses the secured device in step S64. After the user has finished using the secured device, the user terminates body contact with the secured device in step S66. This will prevent the secured device 50 from receiving the ultrasound activation signal, as explained above in connection with FIG. 3.

In some of the preferred embodiments described above, the activation unit 10 is incorporated into a housing that is worn against the user's body, similar to a wristwatch. But a wide variety of alternative approaches for acoustically coupling the activation unit 10 to the user's body can be readily envisioned. Examples include, but are not limited to bracelets, necklaces, a sticky patch worn on the skin, undergarments, shoes, an implant, etc.

Optionally, the activation unit 10 may be incorporated into a multifunction device. For example, the activation unit 10 may be incorporated into a smart watch that has the ability to tell time, send text messages, make phone calls, etc.

Notably, the FIGS. 1-3 embodiment provides at least two independent layers of security. The first layer relies on the requirement for both the activation unit 10 and the secured device 50 to be in contact with the ultrasound conductive body 30 for the ultrasound activation signal to reach the secured device. As a result, controlling access to the activation unit 10 will prevent the vast majority of unauthorized people from operating the secured device 50. Second, even if an unauthorized party (e.g., a criminal, terrorist, etc.) recognizes the nature of the security system that is being used, they will be unable to activate the secured device unless they know the nature of the specific ultrasound activation signal that is expected by the ultrasound receiver 55 in the secured device 50. Optionally, additional layers of security may be obtained by encoding and/or encrypting the ultrasound activation signal, and having the ultrasound receiver 55 ignore all signals that do not match the expected pattern or code.

Although the FIGS. 1-3 embodiment is described above in the context of a financial transaction card and a handgun, it can also be used in a wide variety of alternative contexts. Examples of alternative secured devices include but are not limited to, electronic keys, cards that are used to open doors and the like instead of keys, cell phones, computers, keyboards, voice recorders, cameras, steering wheels, car doors, ignition switches, game consoles, hand held remote controllers (e.g., for televisions), on/off switches of devices or networks, such as light sources, air-conditioning systems, security systems, locks for handbags, suitcases, or luggage, etc.

Note that in addition to the transmission of the ultrasound activation signal from the first ultrasound transducer 19 in the activation unit 10 to the second ultrasound transducer 51 in the secured device 50, those same transducers may be used to convey information in the opposite direction. This may be accomplished by replacing both the signal generator 15 and the ultrasound receiver 55 replaced with transceivers, and making appropriate modifications to the controllers in the activation unit 10 and the secured device 50. This ability to implement bidirectional communication may be useful for providing additional security (e.g., by implementing a data handshaking procedure between the activation unit 10 and the secured device 50), as will be appreciated by persons skilled in the relevant arts.

In some embodiments, both the activation unit 10 and the secured device 50 are powered by batteries (not shown). In alternative embodiments, the secured device 50 receive power from an external source (e.g., via inductive coupling or harvesting of the ultrasound energy that is beamed into the secured device 50).

Although the FIGS. 1-3 embodiment is described above primarily in the context of handheld secured devices that are enabled only when they are in contact with a human user's body, these embodiments may also be used in alternative contexts that transmit the ultrasound activation signal through other types of ultrasound conductive bodies. Examples include, but are not limited to electronic equipment encased in metal or plastic, etc., and metals in cars bodies. In the latter case, the body of the car can serve as the ultrasound conductive body 30 in FIG. 1, and contact with the ultrasound conductive body would be implemented by placing the activation unit against a designated area on the car's body. A wide variety of alternative contexts can be readily envisioned.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

I claim:

1. A system for preventing unauthorized use of a secured device, the system comprising:
    an activation unit that includes
        a first ultrasound transducer positioned to acoustically couple with an ultrasound conductive body when the activation unit is placed in contact with the ultrasound conductive body, and
        an ultrasound signal generator configured to drive the first ultrasound transducer,
        wherein the first ultrasound transducer and the ultrasound signal generator are configured such that when (a) the first ultrasound transducer is acoustically coupled with the ultrasound conductive body and (b) the ultrasound signal generator drives the first ultrasound transducer, the first ultrasound transducer will transmit an ultrasound activation signal into the ultrasound conductive body, and
        wherein the ultrasound signal generator drives the first ultrasound transducer in a manner that embeds a code into the ultrasound activation signal; and
    a secured device that includes
        hardware that performs a function,
        a second ultrasound transducer positioned to acoustically couple with the ultrasound conductive body prior to use of the secured device, and to generate an output signal responsive to ultrasound energy arriving at the second ultrasound transducer,
        an ultrasound receiver that (a) receives the output signal generated by the second ultrasound transducer (b) determines whether variations in the output signal indicate that the code is present in the ultrasound activation signal, and (c) generates the enable signal when the code is present in the ultrasound activation signal, and
        an interface circuit that receives the enable signal,
        wherein the interface circuit is configured to (a) allow the hardware to perform the function when the enable signal arrives and (b) prevent the hardware from performing the function when the enable signal has not arrived.

2. The system of claim 1, wherein the ultrasound signal generator comprises a first controller that is programmed to impart the code and wherein the ultrasound receiver comprises a second controller that that is programmed to recognize when the code is present.

3. The system of claim 2, wherein the activation unit further includes a user interface, and wherein the first controller is further programmed to wait for unlocking via the user interface before imparting the code.

4. The system of claim 3, wherein the unlocking comprises entry of a password or biometric information via the user interface.

5. The system of claim 1, wherein the enable signal persists for a predetermined time after the ultrasound activation signal has arrived at the second ultrasound transducer.

6. The system of claim 1, wherein the code is embedded into the ultrasound activation signal as part of a sequence of codes, and wherein the enable signal terminates immediately when the sequence of codes ceases to arrive at the second ultrasound transducer.

7. The system of claim 1, wherein the ultrasound activation signal has a frequency between 100 kHz and 5 MHz.

8. The system of claim 1, wherein the ultrasound activation signal has a frequency between 1 MHz and 2 MHz.

9. The system of claim 1, wherein the secured device comprises a firearm and wherein the interface circuit is configured to (a) allow the firearm to fire when the enable signal arrives and (b) prevent the firearm from firing when the enable signal has not arrived.

10. The system of claim 9, wherein the interface circuit comprises a solenoid having a first position that prevents the firearm from firing and a second position that allows the firearm to fire, and wherein the interface circuit controls the position of the solenoid in response to the enable signal.

11. The system of claim 1, wherein the secured device comprises a financial transaction card, and wherein the interface circuit is configured to (a) permit use of the financial transaction card when the enable signal arrives and (b) prevent use of the financial transaction card when the enable signal has not arrived.

12. The system of claim 1, wherein the secured device comprises a computer, and wherein the interface circuit is configured to (a) permit use of the computer when the enable signal arrives and (b) prevent use of the computer when the enable signal has not arrived.

13. The system of claim 1, wherein the secured device comprises a mobile phone, and wherein the interface circuit is configured to (a) permit use of the mobile phone when the enable signal arrives and (b) prevent use of the mobile phone when the enable signal has not arrived.

14. The system of claim 1, wherein the ultrasound activation signal comprises an ultrasound carrier wave and the code is embedded into the ultrasound carrier wave according to an analog modulation scheme.

15. The system of claim 1, wherein the ultrasound activation signal comprises an ultrasound carrier wave and the code is embedded into the ultrasound carrier wave according to a spread spectrum modulation scheme.

16. An apparatus for preventing unauthorized use of a secured device, the apparatus comprising:
   hardware that performs a function;
   an ultrasound transducer positioned to acoustically couple with an ultrasound conductive body prior to use of the secured device, and to generate an output signal responsive to ultrasound energy arriving at the ultrasound transducer;
   an ultrasound receiver that (a) receives the output signal generated by the ultrasound transducer, (b) determines whether variations in the output signal indicate that a code is present in the ultrasound activation signal, and (c) generates the enable signal when the code is present in the ultrasound activation signal; and
   an interface circuit that receives the enable signal,
   wherein the interface circuit is configured to (a) allow the hardware to perform the function when the enable signal arrives and (b) prevent the hardware from performing the function when the enable signal has not arrived.

17. The apparatus of claim 16, wherein the enable signal persists for a predetermined time after the ultrasound activation signal has arrived at the ultrasound transducer.

18. The apparatus of claim 16, wherein the code is embedded into the ultrasound activation signal as part of a sequence of codes, and wherein the enable signal terminates immediately when the sequence of codes ceases to arrive at the ultrasound transducer.

19. The apparatus of claim 15, wherein the ultrasound activation signal comprises an ultrasound carrier wave and the code is embedded into the ultrasound carrier wave according to an analog modulation scheme.

20. The apparatus of claim 15, wherein the ultrasound activation signal comprises an ultrasound carrier wave and the code is embedded into the ultrasound carrier wave according to a spread spectrum modulation scheme.

* * * * *